US005718896A

United States Patent [19]

Allen

[11] Patent Number: 5,718,896
[45] Date of Patent: *Feb. 17, 1998

[54] METHODS FOR THE INHIBITING THE TRANSMISSION OF SEXUALLY TRANSMITTED DISEASES

[75] Inventor: Robert C. Allen, San Antonio, Tex.

[73] Assignee: EOE, Inc., Little Rock, Ark.

[*] Notice: The term of this patent shall not extend beyond the expiration date of Pat. No. 5,565,197.

[21] Appl. No.: 572,666

[22] Filed: Dec. 14, 1995

Related U.S. Application Data

[63] Continuation of Ser. No. 371,585, Jan. 12, 1995, Pat. No. 5,565,197, which is a continuation of Ser. No. 48,647, Apr. 15, 1993, abandoned, which is a continuation-in-part of Ser. No. 660,994, Feb. 21, 1991, abandoned.

[51] Int. Cl.$^6$ ..................................................... A61K 38/44
[52] U.S. Cl. .......................... 424/94.4; 429/94.1; 435/189; 435/192
[58] Field of Search ............................... 424/94.4, 94.1; 435/189, 192

[56] References Cited

U.S. PATENT DOCUMENTS

| | | | |
|---|---|---|---|
| 2,679,533 | 5/1954 | Darragh et al. | 564/282 |
| 4,473,550 | 9/1984 | Rosenbaum et al. | 424/94.4 |
| 4,576,817 | 3/1986 | Montgomery et al. | 424/94.4 |
| 4,588,586 | 5/1986 | Kessler et al. | 424/94.4 |
| 4,726,948 | 2/1988 | Prieels et al. | 424/94.4 |
| 4,937,072 | 6/1990 | Kessler et al. | 424/94.4 |
| 4,996,146 | 2/1991 | Kessler | 435/28 |

FOREIGN PATENT DOCUMENTS

| | | |
|---|---|---|
| 098073 | 1/1984 | European Pat. Off. . |
| 361908 | 4/1990 | European Pat. Off. . |
| 397227 | 11/1990 | European Pat. Off. . |
| 0500387 A2 | 8/1992 | European Pat. Off. . |
| 2108387 | 5/1983 | United Kingdom . |
| WO 88/02600 | 4/1988 | WIPO . |
| WO 89/12457 | 12/1989 | WIPO . |

OTHER PUBLICATIONS

Klebanoff, "Myeloproxidase–Halide–Hydrogen Peroxide Antibacterial System," *J. Bacteriol.*95:2131–2138, 1968.

Allen, R.C., Dissertation entitled "Studies on the Generation of Electronic Excitation States in Human Polymorphonuclear Leukocytes and their Participation in Microbicidal Activity", Jul. 1973.

Allen, R.C. et al., "Evidence for the Generation of an Electronic Excitation State(s) in Human Polymorphonuclear Leukocytes and its Participation in Bactericidal Activity," *Biochem. and Biophys. Res. Comm.*47(4):679–684, 1972.

Allen, R.C., "Halide Dependence of the Myeloperoxidase–mediated Antimicrobial System of the Polymorphonuclear Leukocyte in the Phenomenon of Electronic Excitation," *Biochem. and Biophys. Res. Comm.*63(3):675–683, 1975.

Allen, R.C., "The Role of pH in the Chemiluminescent Response of the Myeloperoxidase–Halide–HOOH Antimicrobial System," *Biochem. and Biophys. Res. Comm.*63(3):684–691, 1975.

Allen, R.C., et al., "Phagocytic Activitation of a Luminol–Dependent Chemiluminescense in Rabbit Alveolar and Peritoneal Macrophages," *Biochem. and Biophys. Res. Comm.*69(1):245–252, 1976.

Allen, R.C., "Evaluation of Serum Opsonic Capacity by Quantitating the Initial Chemiluminescent Response from Phagocytizing Polymorphonuclear Leukocytes," *Infection and Immunity*15(3):828–833, 1977.

Allen, R.C. et al., "Correlation of Metabolic and Chemiluminescent Responses of Granulocytes from Three Female Siblings with Chronic Granulomatous Disease," *Journal of Infectious Diseases*136(4):510–518, 1977.

Allen, R.C., "Reduced, radical, and excited state oxygen in leukocyte microbicidal activity," In *Lysosomes in Applied Biology and Therapeutics*, J.T. Dingle et al. (eds.), North–Holland Publishing Co., pp. 197–233, 1979.

Allen, R.C., "Chemiluminescence: An Approach to the Study of the Humoral–phagocyte Axis in Host Defense Againist Infection," In *Liquid Scintillation Counting, Recent Applications and Development, Sample Preparation and Applications*, Academic Press, Inc., 2:377–393, 1980.

Allen, R.C. et al., "Role of Myeloperoxidase and Bacterial Metabolism in Chemiluminescence of Granulocytes from Patients with Chronic Granulomatous Disease," *Journal of Infectious Diseases*144(4):344–348, 1981.

Allen, R.C. et al., "Humoral–Phagocyte Axis of Immune Defense in Burn Patients," *Archives of Surgery*117:133–140, 1982.

Allen, R.C., "Direct Quantification of Phagocyte Activity in Whole Blood: A Chemiluminigenic Probe Approach," In *Proceedings of XI International Congress of Clinical Chemistry, Vienna, 1981*, E. Kaiser et al. (eds.), Walter deGruyter, Berlin, New York, pp. 1043–1058, 1982.

Allen, R.C., "Biochemiexcitation: Chemiluminescence and the Study of Biological Oxygenation Reactions," In *Chemical and Biological Generation of Excited States*, W. Adam et al. (eds.), Academic Press, New York, New York, pp. 309–344, 1982.

(List continued on next page.)

*Primary Examiner*—Jean C. Witz
*Attorney, Agent, or Firm*—Christensen O'Connor Johnson & Kindness PLLC

[57] ABSTRACT

Methods and compositions for the prophylaxis and/or treatment of sexually transmitted diseases (STDs) are disclosed, in which amounts of a haloperoxidase, such as myeloperoxidase or eosinophil peroxidase, and a semen substrate-specific oxidase are administered to a human or animal subject in the environment of sexually transmitted fluids. In the presence of semen, the semen substrate-specific oxidase catalyzes the production of hydrogen peroxide, which in turn is utilized by the haloperoxidase to selectively inhibit pathogenic microbes present in the sexually transmitted fluids. At high concentration levels, the compositions additionally exhibit spermicidal properties.

14 Claims, No Drawings

OTHER PUBLICATIONS

Allen, R.C., "Chemiluminescence and the Study of Phagocyte Redox Metabolism," In *Biochemistry and Function of Phagocytes*, F. Rossi et al. (eds.), Plenum Publishing Corp., pp. 411–421, 1982.

Allen, R.C. et al., "Kinetic Analysis of Microbe Opsonification Based on Stimulated Polymorphonuclear Leukocyte Oxygenation Activity," *Infection and Immunity* 45(2):475–482, 1984.

Allen, R.C., "Phagocytic Leukocyte Oxygenation Activites and Chemiluminescence: A Kinetic Approach to Analysis," In *Methods in Enzymology, Bioluminescence and Chemiluminescence*, M.A. DeLuca et al. (eds.), Academic Press, Inc. 133:449–493, 1986.

Allen, R.C., "Oxygen–Dependent Micobe Killing by Phagocyte Leukocytes: Spin Conservation and Reaction Rate," In the Role of Oxygen in Chemistry and Biochemistry, Proceedings of an International Symposium on Activation of Dioxygen and Homogeneous Catalytic Oxidations, Tsukuba, Japan, Jul. 12–16, 1987, W. Ando et al. (eds.), Elsevier Science Publishers B.V., Amsterdam, *Studies in Organic Chemistry*, 33:425–434, 1988.

Steinbeck, M.J. et al., "Neutrophil Activation by Recombinant Cytokines," *Reviews of Infectious Diseases* 11(4):549–568, 1989.

Malech, H.L. et al., "Medical Intelligence, Neutrophils in Human Diseases," *New England Journal of Medicine* 317(11):687–694, 1987.

Olsson, I. et al., "The Role of the Human Neutrophil in the Inflammatory Reaction," *Allergy* 35:1–13, 1980.

Chenoweth, D.E., "Complement Mediators of Inflammation," In *Immunobiology of the Complement System, An Introduction for Research and Clinical Medicine*, G.D. Ross(ed.), Academic Press, Inc. pp. 63–86, 1986.

Fearon, D.T. et al., "Increased Expression of C3b Receptors on Polymorphonuclear Leukocytes Induced by Chemotactic Factors and by Purification Procedures," *J. Immunology* 130(1): 170–175, 1983.

Fearon, D.T. et al., "Complement Ligand–Receptor Interactions that Mediate Biological Responses," *Ann. Rev. Immunol.* 1:243–271, 1983.

Kearns, D.R. et al., "Sensitized Photooxygenation Reactions and the Role of Singlet Oxygen," *Photochemistry and Photobiology* 10:193–210, 1969.

Kanofsky, J.R., "Singlet Oxygen Production by Lactoperoxidase," *J. Biol. Chem.* 258(10):5991–5993, 1983.

Lehrer, R.I., "Antifungal Effects Peroxidase Systems," *J. Bacteriol.* 99(2):361–365, 1969.

Klebanoff, S.J. et al., "The Peroxidase–Thiocyanate–Hydrogen Peroxide Antimicrobial System," *Biochimica et Biophysica Acta* 117:63–72, 1966.

Klebanoff, S.J., "Myeloperoxidase–Halide–Hydrogen Peroxide Antibacterial System," *J. Bacteriol.* 95(6):2131–2138, 1968.

Klebanoff, S.J., "Myeloperoxidase–mediated Antimicrobial Systems and their Role in Leukocyte Function," reprinted from *Biochemistry of the Phagocytic Process*, Julius Schultz (ed.), North–Holland Publishing Co., 1970.

Klebanoff, S.J. et al., "Toxic Effect of the Peroxidase–Hydrogen Peroxide–Halide Antimicrobial System on *Mycobacterium leprae*," *Infect. and Immun.* 44(2):534–536, 1984.

Hamon, C.B. et al., "A Peroxidase–mediated, Streptococcus mitis–dependent antimicrobial system in saliva," *J. exp. Med.* 137:438–450, 1973.

Steele, W.F. et al., "Antistreptococcal Activity of Lactoperoxidase," *Bacteriol.* 97(2):635–639, 1969.

Mickelson, M.N., "Effect of Lactoperoxidase and Thiocyanate on the Growth of *Streptococcus pyogenes* and *Streptococcus agalactiae* in a Chemically Defined Culture Medium," *J. Gen. Microbiol.* 43:31–43, 1966.

Biosis abstract only, Clark et al., "Peroxidase–H2O2–halide system: Cytotoxic effect on mammalian tumor cells," *Blood* 45(2):161–170, 1975.

Biological Abstract No. 6521608; Rosen, H. et al., "Formation of Singlet oxygen by the Myelo Peroxidase Mediated Antimicrobial System," *J. Biol. Chem.* 252(14):4803–4810, 1977.

Biological Abstract No. 820779537; Thomas E.L. et al., "Oxidation of Chloride and thiocyanate by isolated leukocytes," *J. Biol. Chem.* 261(21):9694–9702, 1986.

Belding, M.E. et al., "Peroxidase–Mediated Virucidal Systems," *Science* 167:195–196, 1970.

Klebanoff, S.J. et al. "Virucidal Activity of $H_2O_2$–generating Bacteria: Requirement for Peroxidase and a Halide," *Journal of Infectious Diseases* 129(3):345–348, 1974.

Klebanoff, S.J. et al., "Viricidal Effect of *Lactobacillus acidophilus* on Human Immunodeficiency Virus Type 1: Possible Role in Heterosexual Transmission," *J. Exp. Med.* 174:289–292, 1991.

Moguilevsky, N. et al., "Lethal oxidative damage to human immunodeficiency virus by human recombinant myeloperoxidase," *Federation of European Biochemical Societies* 302(3):209–212, 1992.

Klebanoff, S.J. et al., "The Source of $H_2O_2$ for the Uterine Fluid–mediated Sperm–Inhibitory System," *Biology of Reproduction* 3:236–242, 1970.

International Search Report in related international application PCT/US94/03089.

Chemical Abstracts No. 136519d, 3(17):233 (1985); Ageta T. et al., "Determination of Free Choline in Human Semen Using an Isotachophoretic Analyzer," *J. Chromatogr.* 343(1):186–189, 1985.

Chemical Abstracts No. 96628n, 74(13):216, 1971; Smith, D.C. et al., "Uterine Fluid–Mediated Sperm–Inhibitory System," *Biol. Reprod.* 3(2):229–235, 1970.

Fahey et al., Status of immune–based therapies in HIV infection and AIDS, Clin. exp. Immunol., vol. 88, pp. 1–5, 1992.

Fox, No winners agaisnt AIDS, Bio/Technology, vol. 12, p. 128, Feb. 1994.

METHODS FOR THE INHIBITING THE TRANSMISSION OF SEXUALLY TRANSMITTED DISEASES

This is a continuation of the prior application Ser. No. 08/371,585, filed on Jan. 12, 1995, of Robert C. Allen for METHODS AND COMPOSITIONS FOR THE PREVENTION OR TREATMENT OF SEXUALLY TRANSMITTED DISEASES, now U.S. Pat. No. 5,565,197 which in turn is a continuation of application Ser. No. 08/048,647 filed on Apr. 15, 1993, now abandoned, which in turn is a continuation-in-part of application Ser. No. 07/660,994 filed on Feb. 21, 1991, now abandoned, the benefit of the filing dates of which are hereby claimed under 35 U.S.C. §120.

FIELD OF THE INVENTION

The present invention relates to methods and compositions for the prevention or treatment of sexually transmitted diseases. More particularly, the invention relates to methods and compositions using oxidase-haloperoxidase microbicidal activity which is activated by a substrate present in semen. The system is highly efficient and directed in that the binary components required for microbicidal action, i.e., the oxidase-haloperoxidase and a semen substrate for the oxidase, are combined at the time of sexual activity.

BACKGROUND OF THE INVENTION

Sexually transmitted diseases (STDs) rank among the most common communicable diseases in the world. Despite organized attempts to educate the public, STDs—such as nonspecific urethritis, chlamydial infections, genital and anorectal herpes and warts, syphilis, gonorrhea, chancroid, and granuloma inguinale—continue to represent a significant public health problem. For gonorrhea, it is estimated that greater than 250 million persons worldwide, and close to 3 million in the United States, are infected annually. For syphilis, annual worldwide incidence is estimated at 50 million persons, with 400,000 in the United States annually needing treatment. Other infections, including salmonellosis, shigellosis, campylobacter, hepatitis A, B and C, and cytomegalovirus infection, sometimes are sexually transmitted. Strong associations between cervical cancer and herpes viruses and papillomaviruses have been discovered. More recently, the spread of human immunodeficiency virus (HIV) resulting in fatal acquired immunodeficiency syndrome (AIDS) has spread rapidly in homosexual and heterosexual groups.

STD incidence has risen despite advances in the diagnosis and treatment of these diseases. Factors that have contributed to this trend include changes in sexual behavior, e.g., widespread used of contraceptive pills and devices; more varied sexual practices, including orogenital and anorectal contact; emergence of strains of organisms less sensitive to antibiotics; symptomless carriers of infecting agents; a highly mobile population; a high level of sexual activity involving multiple partners; ignorance of the facts by physicians and the public; and reticence of patients in seeking treatment.

Conventional treatment of STDs has generally been limited to the administration of antibiotic, antifungal or antiviral drugs, such as tetracycline, penicillin, metronidazole, nystatin, miconazole, sulphamethoxazole and acyclovir, after the transmission and diagnosis of the STD has been made. Conventional prophylaxis for STDs has generally been limited to the use of physical barriers, such as condoms, that prevent or diminish the exchange of bodily fluids during sexual intercourse. Although certain advances have been made in the diagnosis and treatment of STDs, a strong need exists for new methods and compositions that prevent infection by pathogenic microbes during and immediately following sexual activity. Even in the case of curable STDs, prevention is highly preferable to symptomic diagnosis and treatment.

SUMMARY OF THE INVENTION

It has now been discovered that sexually transmitted diseases can be prevented or treated by administering to a human or an animal in the environment of sexually transmitted fluids amounts of a haloperoxidase and a semen substrate-specific oxidase which are effective, in the presence of semen, to inhibit the transmission and colonization of pathogenic microbes present in the sexually transmitted fluids. In the presence of semen, the semen substrate-specific oxidase catalyzes the production of hydrogen peroxide, which in turn is utilized by the haloperoxidase to selectively inhibit pathogenic microbes present in the sexually transmitted fluid without destroying the normal vaginal flora. As such, the present invention provides an antimicrobial system effective against sexually transmitted pathogenic microbes that is activated by sexual activity. The haloperoxidase/semen substrate-specific oxidase system of the invention may optionally be employed at relatively high concentration levels to obtain spermicidal properties.

Suitable haloperoxidases for use in the methods and compositions of the invention include myeloperoxidase (MPO) and eosinophil peroxidase (EPO), while suitable semen substrate-specific oxidases include choline oxidase, cholesterol oxidase, l-amino acid oxidase, polyamine oxidase, urate oxidase (uricase), pyruvate oxidase and lactate oxidase.

DETAILED DESCRIPTION OF THE PREFERRED EMBODIMENT

The present invention is directed to methods and compositions for treating a human or animal to inhibit sexually transmitted disease by administering to the human or animal amounts of a haloperoxidase and a semen substrate-specific oxidase which are effective, in the presence of semen, to inhibit the transmission and colonization of pathogenic microbes. In the practice of the invention, the haloperoxidase and the semen substrate-specific oxidase are provided in the environment of transmitted seminal fluids in a manner in which the antimicrobial properties of the oxidase-haloperoxidase system are triggered by the presence of semen. As a result, maximum microbicidal action is temporally linked to the period of maximum infectious exposure.

Haloperoxidases useful in the present invention are defined as halide:hydrogen peroxide oxidoreductases (e.g., EC No. 1.11.1.7 and EC No. 1.11.1.10 under the International Union of Biochemistry) for which halide is the electron donor or reductant and peroxide is the electron receiver or oxidant. As described in detail in PCT International Publication No. WO 92/14484, the disclosure of which is incorporated herein by this reference, mammalian haloperoxidases, such as myeloperoxidase (MPO) and eosinophil peroxidase (EPO), can be used to selectively bind to and, in the presence of peroxide and halide, inhibit the growth of target microbes without eliminating desirable microbes or significantly damaging other components, such as host cells, in the environment of the target microbe. When a target microbe (e.g., pathogenic bacterium, fungus, or virus) has a binding capacity for haloperoxidase greater than that of the desired microbe (e.g., member of the normal flora) or normal host cells, the target microbe selectively binds the haloperoxidase with little or no binding to the normal flora or normal host cells. In the presence of peroxide and halide, the target-bound haloperoxidase catalyzes halide oxidation and facilitates the disproportionation of peroxide to yield singlet molecular oxygen at the surface of the target microbe in accordance with the following reaction:

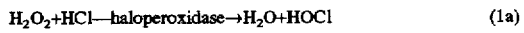
$$H_2O_2 + HCl \xrightarrow{haloperoxidase} H_2O + HOCl \quad (1a)$$

$$H_2O_2 + HOCl \rightarrow H_2O + HCl + {}^1O_2 \quad (1b)$$

The lifetime of singlet molecular oxygen restricts its reactivity and associated damage to within a 0.2 micron radius of the haloperoxidase generator. As such, damage is restricted to the surface of the target microbe. Thus there is selective killing of the target microbe with minimum collateral damage to desired microbes or normal host cells.

Since the antimicrobial activity of the haloperoxidase requires the presence of a peroxide, it has now been discovered that antimicrobial activity can be linked to and triggered by sexual activity when the haloperoxidase is presented together with an oxidase or oxidases which act upon one or more components of semen to produce peroxide. As such, the practice of the invention provides maximum microbicidal action during the time period of maximum exposure to the infecting microbe. Sexual activity is thereby effectively linked to microbicidal action since a compound in the transferred body fluid (i.e., semen) is the rate limiting substrate for an oxidase present in the compositions of the invention. The oxidase-generated peroxide is the rate limiting substrate for haloperoxidase mediated microbicidal action.

Semen substrate-specific oxidases useful in the practice of the invention can be any oxidase capable of utilizing a component of semen as a substrate in the production, either directly or indirectly, of hydrogen peroxide in the environment of transmitted seminal fluids and semen. Semen or ejaculum is a complex viscid fluid of the male reproductive tract consisting of spermatozoa suspended in secretions of the accessory reproductive glands including the testes, epididymides, vas deferens, seminal vesicles, prostate, Cowper's and Littre's glands. The ejaculum can be divided into three major portions. The first portion is prostatic secretion free of spermatozoa and is characterized by a high content of acid phosphatase. The second or middle portion contains spermatozoa, the product of testicular and epididymal secretion. The final portion contains the viscous secretions of the seminal vesicles.

A prostatic proteinase acting on a fibrinogen-like protein from the seminal vesicles is responsible for the coagulation of the semen that immediately follows ejaculation. After a period of approximately ten minutes, this coagulum is in turn liquefied by the action of a plasmin-like prostatic enzyme, and the clot fragments are further hydrolyzed to peptides and amino acids by the action of a chymotrypsin-like enzyme.

The total ejaculate volume is 3.4±1.6 ml. 13–33% of the ejaculate originates from the prostate, 46–80% from the seminal vesicles, and about 10% from the epididymides. The pH of the total ejaculate is in the 6.9 to 7.4 range, and the chloride concentration ranges from 28 to 57 mEq/L.

The ejaculate contains several nitrogenous organic compounds of interest with respect to the invention. The choline content of the total ejaculate is relatively high at 5.8 mM (i.e., 0.7 mg/ml) when determined two minutes after ejaculation. More importantly, the concentration of choline continues to rise for several hours after ejaculation. The additional choline is generated by the action of acid phosphatase, a component of the prostatic portion, on phosphorylcholine. Glycerylphosphorylcholine is also present in the range of 2.1 to 3.5 mM, but is relatively stable to hydrolysis (Arrata et al., 1978, Fert Ster 30:329–333).

Amino acids are generated by the action of proteases. By 4 to 6 hours after ejaculation the amino acid concentration has increased to approximately 12 mg/ml. Several polyamines, originating in the prostatic secretion, are present in the ejaculate. The spermine concentration ranges from 0.3 to 7 mM. Putrescine and spermidine are also present in lower concentrations. Uric acid, an end product of purine metabolism, is present at a concentration of approximately 0.4 mM.

The ejaculate contains a spectrum of carbohydrates and metabolites that are of interest with respect to the present invention. These include citrate (~18 mM), fructose (~13 mM), sialic acid (~3 mM), fucose (~3 mM), pyruvate (3 mM), lactate (~3 mM), and glucose (~0.3 mM). Galactose and sorbitol are also present. Ascorbic acid is present in the range of 0.1 to 0.4 mM. Cholesterol, a lipid of interest with respect to the present invention, is present in the ejaculate at a concentration of 1.6 mM.

The ejaculate is normally transmitted to the environment of the vagina during sexual intercourse. Like skin, the surface of the vagina is stratified squamous epithelium overlying deeper connective tissue, but unlike normal skin there are no hair follicles, sebaceous glands or sweat glands. The term "vaginal mucosa" is incorrect in that this surface does not secrete mucus. However, droplets of transudate-like mucoid fluid appear at the surface of the vaginal epithelium during sexual excitement. These droplets coalesce to form a smooth lubricating surface that facilitates coitus. Sexual stimulation results in blood stasis within the venous plexus investing the vagina. This vasocongestion is believed to be the source of the lubricating transudate.

The vaginal epithelium is composed of a basal layer of germinal epithelium adjacent to the basement membrane. This basalar layer is ~10 microns thick. Above this is the ~14 microns thick parabasalar layer. The intermediate layer is approximately ten cells thick, and during ovulation is the thickest layer (~100 microns) of the epithelium. The cells of the transitional layer, also approximately ten cells thick (~80 microns), show the change from oval to squamous configuration. The superficial layer is composed of approximately ten layers of squamous cells. These outer layers of epithelium serve as a protective barrier against the short lived reactants generated by haloperoxidases.

These squamous cells ultimately cornify, degenerate, desquamate and accumulate in the vagina where they mix with Döderlein bacilli, vaginal transudate and cervical mucus to form an acidic fluid resembling curdled milk. This fluid is the normal secretion of the vagina. The quantity of secretion, estimated by weighing the material absorbed by swabbing the entire vaginal wall, is 0.76±0.04 g (Stone & Gable, 1959). The daily weight of vaginal secretion collected by tampons from six hysterectomized women with intact ovaries was 1.9±0.1 g/24 hours.

The vaginal fluid contains carbohydrate, aliphatic acids, proteins, peptides, amino acids and other compounds released by the disintegration of desquamated epithelial cells. Cholesterol, a constituent of cell membranes, is also present (Preti et al., 1977). Epithelial glycogen is the major source of saccharide and aliphatic acids. Glycogenolysis by either host cells or bacteria produces the glucose that is ultimately metabolized to lactic acid by Döderlein's bacillus. "Döderlein's bacillus" is actually a collection of gram-positive lactic acid bacteria including *Lactobacillus acidophilus, L. casei, L. fermentum, L. cellobiosus,* and *Leuconostoc mesenteroides.* These organisms do not synthesize cytochromes and rely on a flavoenzyme-based redox metabolism. The lactic acid product of lactobacilli metabolism is largely responsible for the acidity of the healthy, mature vagina, i.e., pH 4 to 5. Of additional importance with respect to this invention, these lactobacilli also produce hydrogen peroxide ($H_2O_2$).

In the presence of normal vaginal flora, myeloperoxidase and eosinophil peroxidase are effectively microbicidal. These lactic acid bacteria produce sufficient acid and peroxide to insure dynamic haloperoxidase-based microbicidal action against target bacteria, fungi and viruses. However, conditions, such as vaginitis, which alter the flora and decrease both acidity and peroxide production, can diminish the action of myeloperoxidase and eosinophil peroxidase. Ultimately myeloperoxidase/eosinophil peroxidase will support the growth and re-establishment of normal flora, but during the time interval required to reinstate the normal flora, optimum myeloperoxidase/eosinophil peroxidase microbicidal action is limited by the availability of peroxide.

In the practice of the present invention, a haloperoxidase preferably myeloperoxidase or eosinophil peroxidase, is provided in the environment of transmitted seminal fluids or semen, together with a semen substrate-specific oxidase capable of triggering haloperoxidase antimicrobicidal activity and thereby preventing the transmission of disease caused by microbes present in the transmitted fluids. The semen substrate-specific oxidase can be any of the oxidases capable of utilizing a component of semen as a substrate in the production, either directly or indirectly, of hydrogen peroxide in the environment of the transmitted seminal fluids or semen. Due to the composition of semen and the nature of the vaginal environment, as described above, the presently most preferred semen substrate-specific oxidases are selected from the group consisting of choline oxidase, cholesterol oxidase, 1-amino acid oxidase, polyamine oxidase, urate oxidase (uricase), pyruvate oxidase, and lactate oxidase.

In the practice of the invention, the rate of peroxide production in the environment of the transmitted seminal fluids or semen can be controlled by adjusting the activity of the oxidase included in the compositions of the invention. The actual effectiveness of a unit activity of oxidase depends upon the availability of substrate and environmental conditions such as pH. One unit of oxidase activity will generate about 1 µmol of hydrogen peroxide per minute.

In addition to the inhibition or treatment of sexually transmitted diseases, the methods and compositions of the invention can be designed to enhance or diminish the spermicidal properties of the compositions. If sperm viability is a concern, the concentrations of oxidase and haloperoxidase can be decreased to the lowest levels required for effective microbicidal action in order to minimize collateral damage to sperm. If sperm viability is not desired, the oxidase and haloperoxidase concentrations can be increased so that the resulting peroxide generation is sufficient for haloperoxidase-dependent spermicidal action as well as microbe killing. The proximity and intensity of oxygenation activity would be adequate to insure sperm killing even if sperm binding of haloperoxidase is minimal. The short reactive lifetime of singlet molecular oxygen limits the potential for host damage. The thickness of the squamous epithelium protects the viable vaginal tissue from oxygenation damage. The size of myeloperoxidase (about 140,000 daltons) and eosinophil peroxidase (about 74,000 daltons) presents a physical size barrier to the direct vaginal absorption of these haloperoxidases.

Since the antiseptic activity of the haloperoxidase compositions of the invention involves the reaction of peroxide and halide to form hypohalite, and the reaction of peroxide and hypohalite to form singlet molecular oxygen, as described above, the activity of the compositions of the invention is dependent upon the presence, at the site of infection, of a suitable halide. Suitable halides for use in the methods and compositions of the invention may be bromide or chloride. The use, selection, and amount of halide employed in a particular application will depend upon various factors, such as the haloperoxidase used in the antiseptic composition, the desired therapeutic effect, the availability of peroxide and other factors. When the haloperoxidase is myeloperoxidase, the halide may be bromide or chloride. Since chloride is present in essentially all physiological media at levels sufficient to be nonlimiting as the halide cofactor, an external source of chloride is generally not required and thus the presently most preferable halide for use is chloride. When an external source of chloride is desired, the amount of chloride employed will preferably fall in the range of about 10 µmol chloride to about 150 µmol chloride per ml of solution to approximate physiological conditions. When the haloperoxidase is eosinophil peroxidase, chloride is relatively ineffective as a cofactor, and accordingly, the preferred halide is bromide. When included in liquid compositions for topical use, the compositions of the invention may comprise from about 1 nmol bromide to about 20 µmol bromide per ml of liquid composition, more preferably from about 10 nmol bromide to about 10 µmol bromide per ml of liquid composition, and most preferably from about 100 nmol bromide to about 1 µmol bromide per ml of liquid composition.

The ratio of halide to peroxide is an important consideration in formulating an effective microbicidal environment. Accordingly, in addition to ensuring effective levels of halide and peroxide at the situs of microbial attack, as described above, it is preferable to practice the methods of the invention at halide:peroxide ratios that provide optimal microbicidal activity. High halide:peroxide ratios tend to slow the rate of haloperoxidase activity, but the microbicidal efficiency of the system is relatively well maintained. However, very low ratios compromise haloperoxidase action and diminish microbicidal activity.

The methods and compositions of the invention can be used to treat a broad spectrum of sexually transmitted infections by pathogenic microbes, without destroying the normal flora. As used herein, "pathogenic microbes" is intended to include pathogenic bacteria, fungi, viral particles, yeast, chlamydia, or protozoans which do not normally reside in the host or which are capable of causing host pathology, and which are capable of being specifically and selectively bound to and killed by haloperoxidases, as described in detail herein. Sexually transmitted microbes which can remit in pathogenic infection of a host are well known. Thus, the methods and compositions of the invention can be used in the treatment or prophylaxis of sexually transmitted diseases including, for example, gonococcal urethritis, nonspecific urethritis, mucopurulent cervicitis, nonspecific genital infections, chlamydial infections, syphilis, genital candidiasis, chancroid, lymphogranuloma venereum, genital herpes, acquired immunodeficiency syndrome (AIDS), and the like.

The compositions of the invention generally comprise amounts of a haloperoxidase and a semen substrate-specific oxidase which are effective, in the presence of semen, to inhibit the transmission and colonization of pathogenic microbes, together with a pharmaceutically acceptable carrier or vehicle. The semen substrate-specific oxidase and the haloperoxidase can be free, i.e., separate components of the composition. Alternatively, the oxidase and the haloperoxidase can be covalently or non-covalently linked together or otherwise complexed to ensure close physical proximity between peroxide produced by the oxidase and the haloperoxidase. Any pharmaceutically acceptable carrier or vehicle may be generally used to incorporate the oxidase-haloperoxidase system, provided that the carrier does not significantly interfere with the selective binding capabilities of the haloperoxide or with haloperoxidase or oxidase activities. Preferably, the pharmaceutically acceptable carrier or vehicle is in the form of a liquid, jelly, suppository, foam, sponge, troche or the like containing haloperoxidase and oxidase plus sufficient halide, and adjusted to a pH sufficient to insure optimum microbicidal action. The oxidase-haloperoxidase system can be incorporated into: (a) ointments and jellies, (b) inserts (suppositories, sponges, troches, and the like), (c) foams, and (d) douches. The material is preferably introduced into the vagina of a female, or other environment of transmission of semen or seminal fluids, at about the time of, and preferably prior to sexual intercourse. Depending on the strength of the formulation, the system can be employed for the treatment of nonspecific vaginitis, for protection against sexually transmitted diseases, and for prevention of conception. The manner of administration will preferably be designed to obtain direct contact of the antiseptic compositions with sexually transmitted microbes.

For topical applications, the pharmaceutically acceptable carrier may take the form of lubricants, foams, liquids, creams, lotions, or gels, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration. Compositions of the invention may be impregnated into absorptive materials, such as sponges, or coated onto the surface of solid phase materials, such as condoms, to deliver the compositions to the environment of ejaculated seminal fluids or semen during or after sexual intercourse. Other delivery systems of this type will be readily apparent to those skilled in the art.

Solid dosage forms for topical administration include suppositories, powders, and granules. In solid dosage forms, the compositions may be admixed with at least one inert diluent such as sucrose, lactose, or starch, and may additionally comprise lubricating agents, buffering agents and other components well known to those skilled in the art.

Actual dosage levels of haloperoxidase and the semen-substrate specific oxidase in the compositions of the invention may be varied so as to obtain amounts of haloperoxidase and oxidase at the site of sexually transmitted fluids to obtain the desired therapeutic or prophylactic response for a particular haloperoxidase and method of administration. Accordingly, the selected dosage level will depend on the nature and site of infection, the desired therapeutic response, the route of administration, the desired duration of treatment and other factors. Generally, when the haloperoxidase is myeloperoxidase, liquid dosage forms for topical, vaginal, anal or buccal administration will comprise from about 0.1 picomoles (pmol) to about 500 pmol of myeloperoxidase per ml of liquid composition, more preferably from about 1 pmol to about 200 pmol of myeloperoxidase per ml of liquid composition, and most preferably from about 1 pmol to about 50 pmol of myeloperoxidase per ml of liquid composition. Similar dosages of eosinophil peroxidase may be employed. For non-liquid compositions, dosages of either haloperoxidase will generally comprise from about 1 pmol to about 1 nmol of haloperoxidase (myeloperoxidase or eosinophil peroxidase) per gram of composition, more preferably from about 10 pmol to about 500 pmol of haloperoxidase per grain of composition, and most preferably from about 50 pmol to about 250 pmol of haloperoxidase per gram of composition. Within the foregoing general parameters, from about 0.1 pmol to about 20 pmol haloperoxidase (myeloperoxidase or eosinophil peroxidase) per milliliter are preferred for microbicidal action, while from about 20 pmol to about 500 pmol haloperoxidase are preferred for both microbicidal and spermicidal action. While the foregoing dosage ranges represent general guidelines and presently preferred embodiments, the actual microbicidal and spermicidal activity of the system will be highly dependent on oxidase generation of peroxide, the environment of application and other factors.

Oxidase dosage is described in terms of activity and expressed as units. One unit is defined as the quantity of oxidase that generates 1 μmol of hydrogen peroxide per minute. If the availability of substrate in semen is not limiting, the rate of peroxide generation can be adjusted by controlling the activity of the oxidase in the formulation. Oxidase activity is dependent on the type and quantity of substrate available and on environmental factors such as temperature and pH and including components present in the formulation. Generally, liquid (or non-liquid) dosage forms will comprise a sufficient amount of semen substrate-specific oxidase to generate from about 1 nmol to about 2 μmol peroxide per ml (or per gram) per minute when in the presence of semen, and more preferably from about 10 nmol to about 500 nmol peroxide per ml (or gram) per minute. The foregoing amounts correspond to from about 1 milliunit to about 2 units of oxidase activity, and from about 10 milliunits to about 500 milliunits of oxidase activity, respectively. The lower rates of peroxide generation, e.g., from about 1 nmol to about 100 nmol peroxide per minute will generally be effective for microbicidal action, while the higher rates of peroxide generation, e.g., from about 100 nmol to about 2 μmol peroxide per minute are preferred when both microbicidal and spermicidal activity are desired.

As used herein, the term "normal flora" means bacteria which normally reside in or on body surfaces of a healthy host at symbiotic levels. Normal flora include, for example, the lactic acid family of bacteria in the mouth or vagina of human subjects, e.g., Streptococcus (viridans) in the mouth, and *Lactobacillus sp.* (e.g., Tissier's bacillus and Döderlein's bacillus) in the intestines of breast-fed infants, external genitalia, anterior urethra and vagina. Microorganisms which constitute normal flora of a host are well known (e.g., see *Principles and Practice of Infectious Diseases*, supra, New York, pp. 34–36 and 161). It has been found that the haloperoxidases of the invention selectively bind to many pathogenic microbes in preference over normal flora. The human or animal is preferably treated in accordance with the invention with amounts of haloperoxidase and semen substrate-specific oxidase which are ineffective to eliminate normal flora from the human or animal.

EXAMPLES

Example 1

Use of Choline Oxidase with Haloperoxidase

As described above, semen contains approximately 6 mM (6 μmol/ml) choline. Since the average ejaculate volume is 3.5 ml, approximately 21 μmol of choline are delivered in the ejaculate.

Choline is a substrate for choline oxidase (choline:$O_2$oxidoreductase EC 1.1.3.17):

$$\text{choline} + O_2 \xrightarrow{\text{choline oxidase}} \text{betaine aldehyde} + H_2O_2 \quad (2a)$$

$$\text{betaine aldehyde} + O_2 \xrightarrow{\text{choline oxidase}} \text{betaine} + H_2O_2 \quad (2b)$$

Note that two peroxides are formed per choline oxidized to betaine. Bacterial choline oxidase is commercially available. The choline oxidase from Alcaligenes is a flavine adenine dinucleotide enzyme of approximately 70,000 daltons molecular weight. Its Michaelis constant (Km) is 0.9 mM for choline and 6.2 mM for betaine aldehyde (Ohta-Fukuyama et al., 1980, *J Biochem* 88:197–203). The choline oxidase from Arthrobacter is a flavoenzyme of approximately 75,000 daltons with an isoelectric point (pI) of 4.5. Its Km is 1.2 mM for choline and 8.7 mM for betaine aldehyde (Ikuta et al., 1977, *J Biochem* 82:1741–7149).

In addition to choline, the semen contains approximately 14 mM phosphoryl-choline that is converted to choline by the action of acid phosphatase:

$$\text{phosphorylcholine} \xrightarrow{\text{acid phosphatase}} \text{choline} + \text{phosphate} \quad (3)$$

The hydrolysis of semen phosphorylcholine is essentially complete in one hour. As such, the availability of choline continues to increase within the first hour after ejaculation (Arrata et al., 1978, *Fertil Steril* 30:329–333). Within the first hour after ejaculation the total choline, i.e., the initial choline plus hydrolyzed phosphorylcholine, available is approximately 20 µmol/ml of semen or approximately 70 µmol total.

Total choline conversion by choline oxidase would yield 140 µmol hydrogen peroxide. This is a relatively large quantity of peroxide, but choline conversion to peroxide is dependent on the activity of choline oxidase in the formulation, and as such, the rate of peroxide generation can be adjusted by controlling the quantity of choline oxidase in the formulation. Choline oxidase can be adjusted to a concentration yielding a rate of peroxide generation sufficient for microbicidal action but insufficient for spermicidal action. If desired, the choline oxidase concentration could be increased to yield a rate of peroxide generation sufficient for both microbicidal and spermicidal action. Since choline is not a major constituent of the vaginal fluid, choline oxidation dependent oxygenation activity will terminate with exhaustion of the semen choline.

The bacterial, yeast and fungal spore microbicidal capacities of the choline oxidase-myeloperoxidase and choline oxidase-eosinophil peroxidase systems were demonstrated as follows: Reaction mixtures were prepared containing 0.2 units (i.e., 20 µg) choline oxidase from *Alcaligenes sp.* (when present, as indicated), 20 pmol (2.8 µg) porcine myeloperoxidase (Lot#1899201, ExOxEmis Inc., San Antonio, Tex.) or 20 pmol (1.5 µg) porcine eosinophil peroxidase (Lot#1929201, ExOxEmis Inc., San Antonio, Tex.) in 50 mM Acetate Buffer containing 100 mEq/L Cl⁻, 1 mEq/L Br⁻, and 1 mM l-alanine. The pH was adjusted to 7 by addition of 50 mM MOPS buffer. The final concentration of choline was 150 mM (150 µmol/ml). The final volume was 1 ml. The mixtures were inoculated with ~$10^6$ to $10^7$ colony forming units (CFU) of *S. aureus*, *C. albicans* or *A. fumigatus* spores, and were incubated for four hours at 22° C. *S. aureus* was then plated on trypticase soy agar. *C. albicans* and *A. fumigatus* were plated on Sabouraud's dextrose agar. The results are expressed in Table 1 as the CFU's counted after ~48 hours of incubation at 35° C.

TABLE 1

Choline Oxidase-Haloperoxidase Microbicidal Action Against *Staphylococcus aureus*, *Candida albicans*, and *Aspergillus fumigatus*:

| Organism | Choline Oxidase | Haloperoxidase | CFU |
|---|---|---|---|
| *Staph. aureus* | None | None | 19,400,000 |
| *Staph. aureus* | 0.2 Unit | None | 15,400,000 |
| *Staph. aureus* | 0.2 Unit | 20 pmol MPO | 0 |
| *Staph. aureus* | 0.2 Unit | 20 pmol EPO | 0 |
| *Cand. albicans* | None | None | 1,460,000 |
| *Cand. albicans* | 0.2 Unit | None | 1,200,000 |
| *Cand. albicans* | 0.2 Unit | 20 pmol MPO | 0 |
| *Cand. albicans* | 0.2 Unit | 20 pmol EPO | 0 |
| *Asperg. fumigatus* | None | None | 1,260,000 |
| *Asperg. fumigatus* | 0.2 Unit | None | 1,300,000 |
| *Asperg. fumigatus* | 0.2 Unit | 20 pmol MPO | 0 |
| *Asperg. fumigatus* | 0.2 Unit | 20 pmol EPO | 0 |

As shown in Table 1, when substrate (i.e., choline) is not limiting (e.g., 150 mM), 0.2 units (20 µg) of choline oxidase plus either 20 pmol (2.8 µg) myeloperoxidase or 20 pmol (1.5 µg) eosinophil peroxidase is sufficient for complete killing of *Staphylococcus aureus*, *Candida albicans*, as well as *Aspergillus fumagatus* spores. The quantity of choline oxidase-haloperoxidase required for effective spermicidal action must be empirically determined for each type of formulation employing this system.

The direct effect of varying choline oxidase on microbicidal activity against *Staphylococcus aureus* was determined as follows. In order to assess the choline oxidase requirement, the foregoing procedure was followed except that the quantities of choline (40 µmol/ml) and haloperoxidase (10 pmol/ml) were set to lower but still within non-rate-limiting concentrations, and choline oxidase was varied.

Each test contained the indicated quantity of choline oxidase from *Alcaligenes sp.* (0.1 Unit equals 10 µg), 10 pmol (1.4 µg) porcine myeloperoxidase (Lot#1899201) or 10 pmol (0.7 µg) porcine eosinophil peroxidase (Lot#1929201) in 50 mM Acetate Buffer containing 100 mEq/L Cl⁻, 1 mEq/L Br⁻, and 1 mM l-alanine. The pH was adjusted to 6.7 by addition of 50 mM MOPS buffer. The final concentration of choline was 40 mM (40 µmol/ml). The final volume was 1 ml. After two hours incubation (37° C.) the microbes were plated on trypticase soy agar. The results are expressed in Table 2 as the colony forming units (CFU's) counted.

TABLE 2

Effect of Choline Oxidase Concentration on Choline Oxidase-Haloperoxidase Microbicidal Action Against *Staphylococcus aureus*:

| Organism | Choline Oxidase | Haloperoxidase | CFU |
|---|---|---|---|
| *Staph. aureus* | None | None | 23,800,000 |
| *Staph. aureus* | 0.2 Unit | None | 8,200,000 |
| *Staph. aureus* | 0.2 Unit | 10 pmol MPO | 0 |
| *Staph. aureus* | 0.1 Unit | 10 pmol MPO | 0 |
| *Staph. aureus* | 0.05 Unit | 10 pmol MPO | 0 |
| *Staph. aureus* | 0.025 Unit | 10 pmol MPO | 80,000 |
| *Staph. aureus* | None | 10 pmol MPO | 17,000,000 |
| *Staph. aureus* | 0.2 Unit | 10 pmol EPO | 0 |
| *Staph. aureus* | 0.1 Unit | 10 pmol EPO | 0 |
| *Staph. aureus* | 0.05 Unit | 10 pmol EPO | 0 |
| *Staph. aureus* | 0.025 Unit | 10 pmol EPO | 32,000 |
| *Staph. aureus* | None | 10 pmol EPO | 2,400,000 |

As shown in Table 2, complete killing of *Staph. aureus* is observed with 0.05 Units of oxidase, and incomplete but significant killing is observed with 0.025 units of oxidase. Assuming that optimum reaction requirements are met, 50 milliunits (0.05 unit) of oxidase should generate about 50 nmol hydrogen peroxide per minute. Some killing of *Staph. aureus* is also observed with eosinophil peroxidase alone, and to a lesser extent, with choline oxidase alone.

Example 2

Use of Cholesterol Oxidase with Haloperoxidase

The cholesterol concentration of semen is approximately 1.6 mM. Assuming a 3.5 ml volume, there are approximately 5.6 μmol cholesterol per ejaculum. Although difficult to quantify, cholesterol is also a major component of the vaginal fluid (Stone & Gable, 1959).

Cholesterol and other 3β-hydroxy steroids are the substrates for the flavoenzyme cholesterol oxidase (cholesterol:$O_2$ oxidoreductase EC 1.1.3.6):

Cholesterol+$O_2$—cholesterol oxidase→4-cholesten-3-one+$H_2O_2$ (4)

A broad variety of microbial cholesterol oxidases are commercially available. For the present example, *Norcardia erythropolis* cholesterol oxidase was employed. This flavoenzyme is very stable, active over a broad pH range, and has a Km of 14 mM for cholesterol (Richmond, 1973, Clin Chem 19: 1350–1356).

The cholesterol oxidase-haloperoxidase system differs from the previously described choline oxidase-haloperoxidase system in that cholesterol, the substrate for the oxidase, is present in the vaginal fluid prior to exposure to semen. Cholesterol oxidase-haloperoxidase activity is in part independent of semen, and as such, microbicidal action is initiated at the time of application. In the event of sexual intercourse, ejaculation of semen results in the coincident introduction of ~5.6 μmol of cholesterol as substrate for the cholesterol oxidase-haloperoxidase formulation in place in the vagina.

Cholesterol oxidase is a relatively robust enzyme, and as demonstrated by the data of Table 3, the cholesterol oxidase-haloperoxidase system exerts a potent microbicidal action against bacteria, yeast and fungal spores. Even if the combined vaginal plus semen cholesterol does not exceed 6 μmol total, this system should provide adequate protection against sexually transmitted diseases. This system is also potentially spermicidal, but the limitation of substrate suggests that it might be less potent than the choline oxidase-haloperoxidase system in this regard.

To demonstrate the efficacy of compositions of the invention employing cholesterol oxidase as the semen-specific oxidase, the procedure of Example 1 was repeated using cholesterol oxidase as follows. Where indicated the reaction contained 0.1 units (i.e., 4 μg) cholesterol oxidase from *Norcardia erythrolpolis*, 20 pmol (2.8 μg) porcine myeloperoxidase (Lot#1899201, ExOxEmis, Inc., San Antonio, Tex.) or 20 pmol (1.5 μg) porcine eosinophil peroxidase (Lot#1929201, ExOxEmis, Inc., San Antonio, Tex.) in 50 mM Acetate Buffer containing 100 mEq/L Cl⁻, 1 mEq/L Br⁻, and 1 mM l-alanine. The pH was adjusted to 7 by addition of 50 mM MOPS buffer. The final concentration of cholesterol was 7 mM (7 μmol/ml). The final volume was 1 ml. After four hours incubation the microbes were plated. *S. aureus* was plated on trypticase soy agar. *C albicans* and *A. fumigatus* were plated on Sabouraud's dextrose agar. The results are expressed in Table 3 as the colony forming units (CFU's) counted.

TABLE 3

Cholesterol Oxidase-Haloperoxidase Microbicidal Action Against *Staphylococcus aureus*, *Candida albicans*, and *Aspergillus fumigatus*:

| Organism | Cholesterol Oxidase | Haloperoxidase | CFU |
|---|---|---|---|
| *Staph. aureus* | None | None | 19,400,000 |
| *Staph. aureus* | 0.1 Unit | None | 29,200,000 |
| *Staph. aureus* | 0.1 Unit | 20 pmol MPO | 0 |
| *Staph. aureus* | 0.1 Unit | 20 pmol EPO | 0 |
| *Cand. albicans* | None | None | 1,460,000 |
| *Cand. albicans* | 0.1 Unit | None | 1,580,000 |
| *Cand. albicans* | 0.1 Unit | 20 pmol MPO | 0 |
| *Cand. albicans* | 0.1 Unit | 20 pmol EPO | 0 |
| *Asperg. fumigatus* | None | None | 1,260,000 |
| *Asperg. fumigatus* | 0.1 Unit | None | 880,000 |
| *Asperg. fumigatus* | 0.1 Unit | 20 pmol MPO | 0 |
| *Asperg. fumigatus* | 0.1 Unit | 20 pmol EPO | 0 |

Example 3

Use of Alternative Oxidases with Haloperoxidase

The semen contains a number of other compounds that are substrates, or can be modified to serve as substrates, for oxidases yielding peroxide. The more obvious compounds include l-amino acids, polyamines, urate, lactate, pyruvate, glucose and galactose. The concentrations of these compounds in semen are sufficient to drive oxidase-haloperoxidase microbicidal action. Certain of these compounds, such as l-amino acids and polyamines, have advantage with regard to being present in relatively high concentrations.

A number of potential substrates are also present if an additional enzyme is incorporated in the formulation. For example, if an isomerase were found to convert fructose to glucose, inclusion of such an enzyme in a glucose oxidase-haloperoxidase formulation would allow fructose (~13 μmol/ml semen) to serve as an indirect substrate for the generation of peroxide by glucose oxidase. In addition, depriving the spermatozoa of fructose, a major nutrient, is likely to further contribute to the spermicidal capacity of such a system.

Glucose is a major nutrient for Döderlein's bacilli, and as such, glucose is probably not the best substrate for an oxidase-haloperoxidase microbicidal system. Enzymatic depletion of glucose might adversely affect the normal flora. It is far better to have Döderlein's bacilli directly metabolize glucose to lactic acid and peroxide. However, the lactate product of normal flora metabolism can serve as substrate for a lactate oxidase-haloperoxidase microbicidal system.

Lactate is substrate for the flavoenzyme lactate oxidase (lactate:$O_2$ oxidoreductase):

lactate+$O_2$—lactate oxidase→pyruvate+$H_2O_2$ (5)

A commercial lactate oxidase prepared from *Pediococcus sp.* was used in the present example (Mizutani et al., 1983, Anal Chem 55:35–38). As illustrated by the data of Table 4, this lactate oxidase-haloperoxidase system demonstrated good bactericidal activity. However, fungicidal activity is poor in comparison to the other oxidase-haloperoxidase systems tested.

The procedure of Example 1 was repeated using lactate oxidase as the semen-substrate specific oxidase as follows. Where indicated the reaction contained 0.2 units (i.e., 5 μg)

lactate oxidase from *Pediococcus sp.*, 20 pmol (2.8 µg) porcine myeloperoxidase (Lot#1899201, ExOxEmis, Inc., San Antonio, Tex.) or 20 pmol (1.5 µg) porcine eosinophil peroxidase (Lot#1929201, ExOxEmis, Inc., San Antonio, Tex.) in 50 mM Acetate Buffer containing 100 mEq/L Cl⁻, 1 mEq/L Br⁻, and 1 mM. l-alanine. The pH was adjusted to 7 by addition of 50 mM MOPS buffer. The final concentration of lactate was 150 mM (150 µmol/ml). The final volume was 1 ml. After four hours incubation the microbes were plated. *S. aureus* was plated on trypticase soy agar. *C. albicans* and *A. fumigatus* were plated on Sabouraud's dextrose agar. The results are expressed in Table 4 as the colony forming units (CFU's) counted.

TABLE 4

Lactate Oxidase-Haloperoxidase Microbicidal Action Against *Staphylococcus aureus*, *Candida albicans*, and *Aspergillus fumigatus*:

| Organism | Lactate Oxidase | Haloperoxidase | CFU |
|---|---|---|---|
| Staph. aureus | None | None | 19,400,000 |
| Staph. aureus | 0.2 Unit | None | 24,400,000 |
| Staph. aureus | 0.2 Unit | 20 pmol MPO | 0 |
| Staph. aureus | 0.2 Unit | 20 pmol EPO | 0 |
| Cand. albicans | None | None | 1,460,000 |
| Cand. albicans | 0.2 Unit | None | 1,020,000 |
| Cand. albicans | 0.2 Unit | 20 pmol MPO | 1,500,000 |
| Cand. albicans | 0.2 Unit | 20 pmol EPO | 1,180,000 |
| Asperg. fumigatus | None | None | 1,260,000 |
| Asperg. fumigatus | 0.2 Unit | None | 760,000 |
| Asperg. fumigatus | 0.2 Unit | 20 pmol MPO | 400,000 |
| Asperg. fumigatus | 0.2 Unit | 20 pmol EPO | 18,000 |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of inhibiting the transmission of a sexually transmitted disease caused by microbes present in sexually transmitted fluids, comprising:
   contacting said sexually transmitted fluids with a haloperoxidase composition in an amount effective to inhibit said microbes; wherein said composition comprises:
   (a) a haloperoxidase;
   (b) a semen substrate-specific oxidase; and
   (c) a pharmaceutically acceptable carrier.

2. The method of claim 1 wherein said haloperoxidase is selected from the group consisting of myeloperoxidase and eosinophil peroxidase.

3. The method of claim 2 wherein said haloperoxidase is present in said composition in an amount from about 0.1 pmol to about 500 pmol per ml and said pharmaceutically acceptable carrier is a liquid.

4. The method of claim 2 wherein said haloperoxidase is present in said composition in an mount from about 1 pmol to about 200 pmol per ml and said pharmaceutically acceptable carrier is a liquid.

5. The method of claim 2 wherein said haloperoxidase is present in said composition in an amount from about 1 pmol to about 1 nmol per gram and said pharmaceutically acceptable carrier is a non-liquid.

6. The method of claim 2 wherein said haloperoxidase is present in said composition in an amount from about 10 pmol to about 500 pmol per gram and said pharmaceutically acceptable carrier is a non-liquid.

7. The method of claim 1 wherein said semen substrate-specific oxidase is effective to generate from about 1 nmol to about 1 µmol peroxide per ml per minute when in the presence of semen.

8. The method of claim 1 wherein said semen substrate-specific oxidase is effective to generate from about 10 nmol to about 500 nmol peroxide per ml per minute when in the presence of semen.

9. The method of claim 1 wherein said semen substrate-specific oxidase is selected from the group consisting of choline oxidase, cholesterol oxidase, l-amino acid oxidase, polyamine oxidase, urate oxidase, pyruvate oxidase, and lactate oxidase.

10. The method of claim 9 wherein said composition comprises from about 1 milliunit to about 2 units of choline oxidase or cholesterol oxidase per ml and said pharmaceutically acceptable carrier is a liquid.

11. The method of claim 9 wherein said composition comprises from about 1 milliunit to about 2 units of choline oxidase or cholesterol oxidase per gram and said pharmaceutically acceptable carrier is a non-liquid.

12. The method of claim 9 wherein said composition comprises from about 10 milliunits to about 500 milliunits of choline oxidase or cholesterol oxidase per ml and said pharmaceutically acceptable carrier is a liquid.

13. The method of claim 9 wherein said composition comprises from about 10 milliunits to about 500 milliunits of choline oxidase or cholesterol oxidase per gram and said pharmaceutically acceptable carrier is a non-liquid.

14. The method of claim 1 wherein said pharmaceutically acceptable carrier is an ointment, a jelly, a foam, a douche or a vaginal insert.

* * * * *

UNITED STATES PATENT AND TRADEMARK OFFICE
CERTIFICATE OF CORRECTION

PATENT NO. : 5,718,896
DATED : February 17, 1998
INVENTOR(S) : R. C. Allen

It is certified that error appears in the above-identified patent and that said Letters Patent is hereby corrected as shown below:

ON THE TITLE PAGE:

ITEM

[56] Refs. Cited (Other Publs., Item 1)
Pg. 1, col. 1
""Myeloproxidase-Halide-Hydrogen" should read --"Myeloperoxidase-Halide-Hydrogen--

[56] Refs. Cited (Other Publs., Item 10)
Pg. 1, col. 2
"Againist" should read --Against--

[56] Refs. Cited (Other Publs., Item 17)
Pg. 2, col. 1
After "Academic Press, Inc." insert --,--

[56] Refs. Cited (Other Publs., Item 18)
Pg. 2, col. 1
"Micobe" should read --Microbe--

[56] Refs. Cited (Other Publs., Item 27)
Pg. 2, col. 1
Between "Effects" and "Peroxidase" insert --of--

[56] Refs. Cited (Other Publs., Item 32)
Pg. 2, col. 2
"*exp.*" should read --*Exp.*--

UNITED STATES PATENT AND TRADEMARK OFFICE
CERTIFICATE OF CORRECTION

PATENT NO.   :   5,718,896                          Page 2 of 3
DATED        :   February 17, 1998
INVENTOR(S)  :   R. C. Allen It is certified that error appears in the above-identified patent and that said Letters Patent is hereby corrected as shown below:

| COLUMN | LINE | ERROR |
|---|---|---|
| [56] Pg. 2, col. 2 | Refs. Cited (Other Publs., Item 33) | Before "*Bacteriol.*" insert --*J.*-- |
| [56] Pg. 2, col. 2 | Refs. Cited (Other Publs., Item 34) | "*pyogenes*and *Streptococcus agalactiae*in" should read --*pyogenes* and *Streptococcus agalactiae* in-- |
| [56] Pg. 2, col. 2 | Refs. Cited (Other Publs., Item 36) | "6521608;" should read --65021608;-- |
| [56] Pg. 2, col. 2 | Refs. Cited (Other Publs., Item 37) | "820779537;" should read --82079537;-- |
| [56] Pg. 2, col. 2 | Refs. Cited (Other Publs., Item 40) | "*acidophilus*on" should read --*acidophilus* on-- |
| [56] Pg. 2, col. 2 | Refs. Cited (Other Publs., Item 47) | "againist" should read --against-- |

UNITED STATES PATENT AND TRADEMARK OFFICE
CERTIFICATE OF CORRECTION

PATENT NO. : 5,718,896
DATED : February 17, 1998
INVENTOR(S) : R. C. Allen

It is certified that error appears in the above-identified patent and that said Letters Patent is hereby corrected as shown below:

| COLUMN | LINE | |
|---|---|---|
| 6 | 59 | "remit" should read --result-- |
| 8 | 11 | "grain" should read --gram-- |
| 9 | 12 | "(Kin)" should read --(Km)-- |
| 11 | 55 | "*erythrolpolis,*" should read --*erythropolis,*-- |
| 13 | 6 | After "1 mM" delete "." |
| 14 (Claim 4, line 2) | 4 | "mount" should read --amount-- |

Signed and Sealed this

Twentieth Day of April, 1999

Attest:

*Attesting Officer*

Q. TODD DICKINSON

*Acting Commissioner of Patents and Trademarks*